United States Patent
Ohta

(10) Patent No.: US 9,146,179 B2
(45) Date of Patent: Sep. 29, 2015

(54) TEST PIECE TRANSFER APPARATUS

(71) Applicant: ARKRAY, Inc., Kyoto-Shi (JP)

(72) Inventor: Shinichi Ohta, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 445 days.

(21) Appl. No.: 13/714,708

(22) Filed: Dec. 14, 2012

(65) Prior Publication Data

US 2013/0152709 A1 Jun. 20, 2013

(30) Foreign Application Priority Data

Dec. 16, 2011 (JP) .................................. 2011-275385
Oct. 15, 2012 (JP) .................................. 2012-228014

(51) Int. Cl.
*G01N 1/00* (2006.01)
*G01N 33/487* (2006.01)

(52) U.S. Cl.
CPC ............ *G01N 1/00* (2013.01); *G01N 33/48764* (2013.01)

(58) Field of Classification Search
None
See application file for complete search history.

(56) References Cited

U.S. PATENT DOCUMENTS

| 4,924,714 A * | 5/1990 | Gross ......................... 73/863.11 |
| 4,969,738 A * | 11/1990 | Mann ............................. 422/177 |
| 2012/0077274 A1* | 3/2012 | Chiou et al. .................... 436/43 |

FOREIGN PATENT DOCUMENTS

| DE | 0 288 946 | * 11/1988 |
| DE | 198 57 426 | * 6/2000 |
| JP | 2005-127801 A | 5/2005 |
| JP | 2005-201641 A | 7/2005 |

\* cited by examiner

*Primary Examiner* — Robert R Raevis
(74) *Attorney, Agent, or Firm* — Fox Rothschild LLP

(57) ABSTRACT

A test piece transfer apparatus includes a transfer mechanism for transferring a test piece in a transfer direction. The transfer mechanism is provided with a test piece holder for holding the test piece, and with a driving portion. The test piece transfer apparatus further includes a test piece adjusting mechanism cooperating with the transfer mechanism for adjusting the direction of a test piece being transferred. The test piece holder includes a lower surface holding portion, an upstream holding portion and a downstream holding portion. The lower surface holding portion comes into contact with the lower surface of the test piece. The upstream holding portion is arranged on an upstream side of the test piece in the transfer direction. The downstream holding portion is arranged on a downstream side of the test piece in the transfer direction.

9 Claims, 14 Drawing Sheets

TEST PIECE TRANSFER APPARATUS

BACKGROUND OF THE INVENTION

1. Field of the Invention

The present invention relates to a test piece transfer apparatus for transferring a test strip for use in e.g. urine qualitative analysis.

2. Description of the Related Art

FIG. 14 shows an example of conventional test piece transfer apparatus (see Patent Document 1, for example). The test piece transfer apparatus X shown in the figure includes a pair of rollers 91 and a belt 92, and is designed to transfer e.g. a test piece 99 for use in urine qualitative analysis. The test piece transfer apparatus X, along with an analysis unit not shown, may constitute an analyzer. The paired rollers 91 are spaced apart from each other in the direction x, and one of the rollers is driven for rotation in the direction indicated by an arrow in the figure by a driving source such as a motor. The belt 92 is an endless belt made of e.g. rubber and wound around the rollers 91. The upper surface of the belt 92 in the direction z is a transfer surface for transferring the test piece 99 to the left in the direction x. The test piece 99 is in the form of a strip having a width along the direction x and a length along a direction perpendicular to the sheet surface of the figure. The test piece 99 has on the upper surface a plurality of reagent regions (not shown). For instance, a plurality of test pieces 99 are stored on the upper right of the belt 92 in the figure. These test pieces 99 are placed onto a right portion of the transfer surface of the belt 92 one by one and successively transferred to the left in the direction x. The test piece 99 transferred in this way is subjected to e.g. urine qualitative analysis, with e.g. urine as a specimen applied to the reagent region.

To properly apply a specimen such as urine to the reagent region, it is desirable that the test piece 99 is set at a proper position during the transfer. However, in the transfer process, the test piece 99 in the form of a strip easily deviates from the proper position by e.g. turning around an axis extending in the direction z due to paper powder or dust accumulated on the belt 92, for example. Further, when the test piece is placed at an improper position in the direction perpendicular to the sheet surface of the figure, proper application of urine is hindered. Moreover, since urine qualitative analysis is generally performed with respect to a large number of specimens, a faster transfer speed is more desirable. With the conventional structure, however, when the transfer speed is too fast, the front edge of the test piece 99 in the transfer direction may rise from the surface of the belt. In such a case, the test piece 99 cannot be properly transferred to a position for applying urine.

Patent Document 1: Japanese Patent No. 3106351

SUMMARY OF THE INVENTION

The present invention has been proposed under the circumstances described above. It is therefore an object of the present invention to provide a test piece transfer apparatus that ensures smooth transfer of a test piece while preventing the displacement of the test piece being transferred.

According to a first aspect of the present invention, there is provided a test piece transfer apparatus comprising: a transfer mechanism for transferring an elongated test piece in a transfer direction corresponding to a width direction of the test piece, the transfer mechanism being provided with a test piece holder for holding the test piece and with a driving portion; and a test piece adjusting mechanism cooperating with the transfer mechanism for adjusting a direction of the test piece. The test piece holder includes: a lower surface holding portion for coming into contact with a lower surface of the test piece; an upstream holding portion arranged on an upstream side of the test piece in the transfer direction; and a downstream holding portion arranged on a downstream side of the test piece in the transfer direction.

According to a second aspect of the present invention, the test piece holder may comprise a plurality of test piece holding members spaced apart from each other along the test piece.

According to a third aspect of the present invention, in the transfer apparatus of the first or second aspect, the test piece holder may come into holding contact with the test piece at a position spaced apart from each of two ends of the test piece.

According to a fourth aspect of the present invention, in the transfer apparatus of the first through third aspects, the upstream holding portion may comprise a wall surface facing the test piece, where the wall surface forms an acute angle with respect to the transfer direction.

According to a fifth aspect of the present invention, in the transfer apparatus of the first through fourth aspects, the test piece adjusting mechanism may include a flat portion and a raised portion arranged on a downstream side of the flat portion in the transfer direction, and the flat portion may be at a lower position than the lower surface holding portion, and the raised portion may be raised above the lower surface holding portion.

According to a sixth aspect of the present invention, in the transfer apparatus of the fifth aspect, the downstream holding portion may be smaller in height than the upstream holding portion, and the raised portion may be raised to a point that is higher than the downstream holding portion and lower than an upper end of the upstream holding portion.

According to a seventh aspect of the present invention, in the transfer apparatus of the fifth or sixth aspect, the test piece holder may comprise two test piece holding members spaced apart from each other along the test piece with a center of the test piece being sandwiched by the two test piece holding members, and the raised portion may be arranged between the two test piece holding members.

According to an eighth aspect of the present invention, in the transfer apparatus of the first aspect, the test piece adjusting mechanism may be provided with a first position adjusting section and a second position adjusting section disposed on a downstream side of the first position adjusting section in the transfer direction, and also with a first and a second longitudinal position adjusting surfaces spaced apart from each other in a longitudinal direction of the test piece. In the first position adjusting section, the first longitudinal position adjusting surface and the second longitudinal position adjusting surface may face each other in such a manner that a distance between the first and the second longitudinal position adjusting surfaces reduces as proceeding downward in the transfer direction. The first longitudinal position adjusting surface may be present in the second position adjusting section, and the second longitudinal position adjusting surface as a whole may be disposed out of the second longitudinal position adjusting surface.

According to a ninth aspect of the present invention, in the transfer apparatus of the eighth aspect, each of the first and the second longitudinal position adjusting surfaces may be inclined with respect to the transfer direction.

According to a tenth aspect of the present invention, in the transfer apparatus of the eight or ninth aspect, the flat portion may be arranged to overlap, along the transfer direction, at least one of the first position adjusting section and the second position adjusting section, and the raised portion may include a part that is positioned on the downstream side of the second position adjusting section in the transfer direction so as not to overlap the second position adjusting section.

According to the present invention, a test piece can be transferred with the lower surface holding portion holding the test piece from below, with the upstream holding portion being positioned on the upstream side of the test piece in the transfer direction, and with the downstream holding portion being positioned on the downstream side of the test piece in the transfer direction. Thus, the test piece is prevented from unduly rotating about a vertical axis. Thus, the test piece can be transferred smoothly without undergoing positional deviation.

Other features and advantages of the present invention will become clearer from the detailed description given below with reference to the accompanying drawings.

DETAILED DESCRIPTION OF THE PREFERRED EMBODIMENTS

Preferred embodiments of the present invention are described below with reference to the accompanying drawings.

Figure 1:
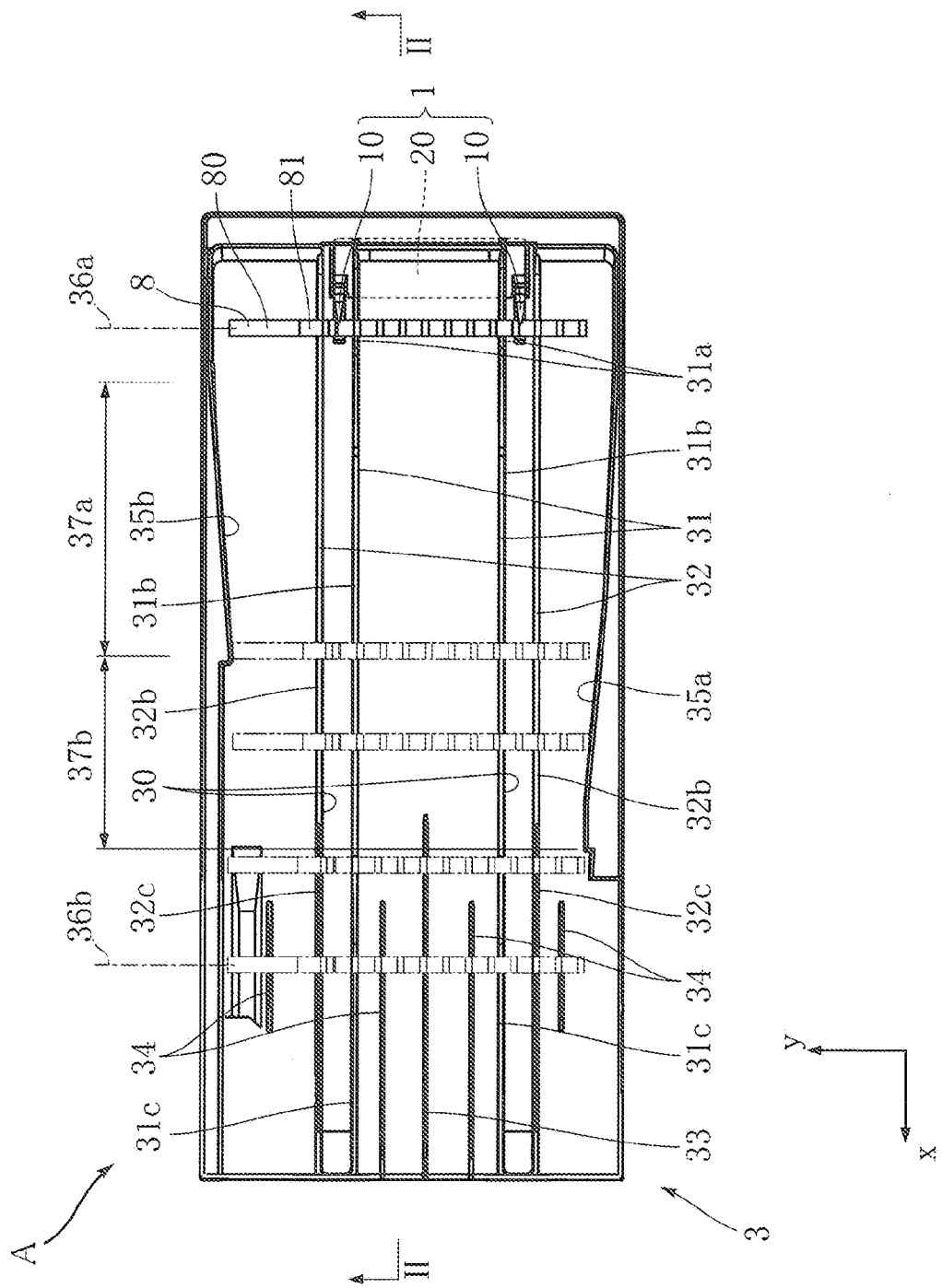
FIG. 1 is a plan view showing a test piece transfer apparatus according to a first embodiment of the present invention.
Figure 2:
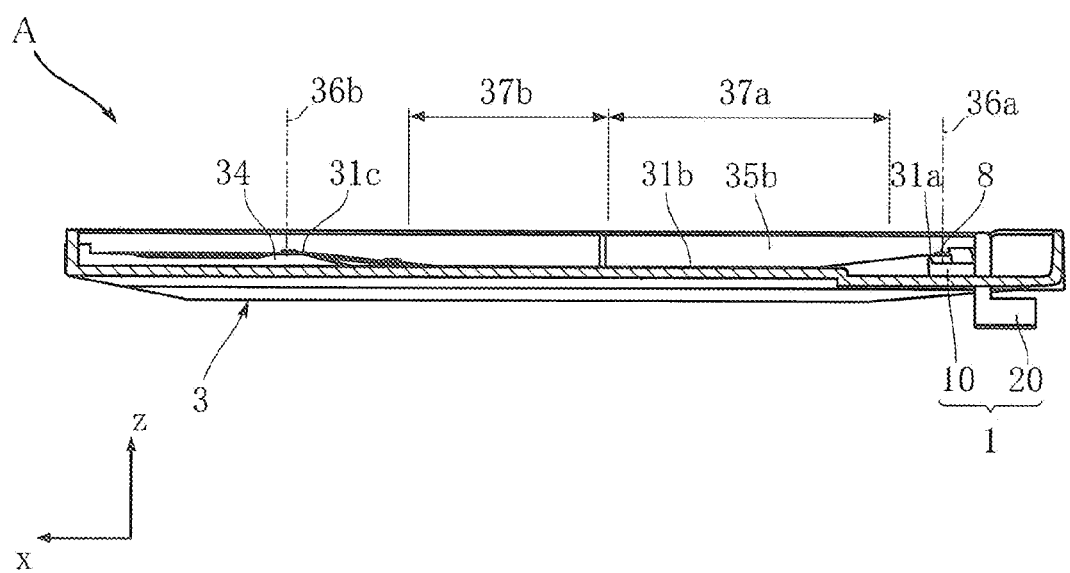
FIG. 2 is a sectional view taken along lines II-II in FIG. 1.

FIGS. 1 and 2 show a test piece transfer apparatus according to an embodiment of the present invention. The illustrated test piece transfer apparatus A1 includes a transfer mechanism 1 and a base body (or cover) 3. The transfer apparatus A1 may transfer an elongated test piece 8 for e.g. urine qualitative analysis in the direction x. A plurality of test pieces 8 may be stored on an upper right side in FIG. 1. These test pieces 8 are transferred by the transfer apparatus A1 one by one to the left in the direction x. The test piece 8 transferred is subjected to e.g. urine qualitative analysis, with urine as a specimen applied to a reagent region, which will be described later. The transfer apparatus A1 may constitute part of an analyzer for performing e.g. urine qualitative analysis.

Figure 3:
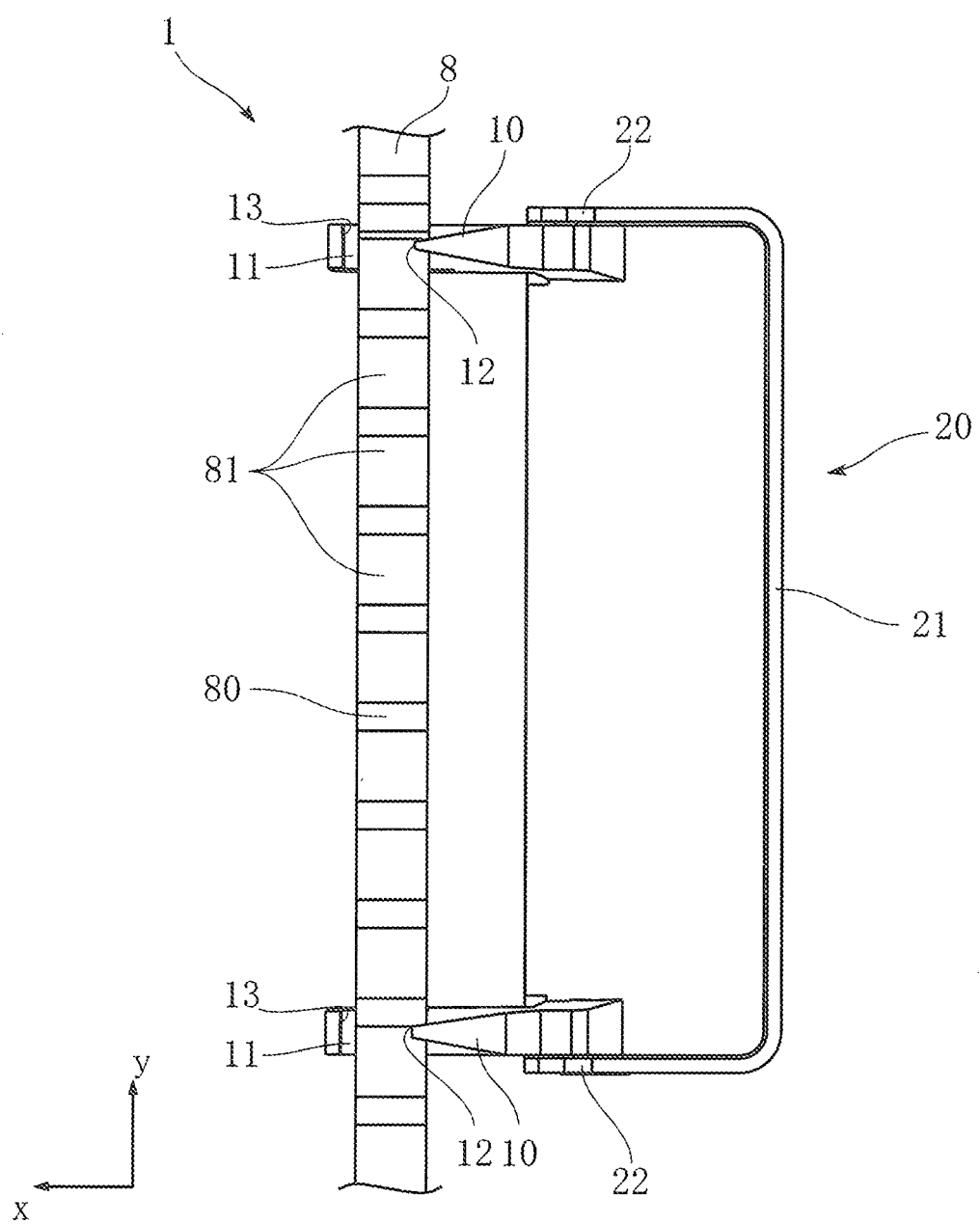
FIG. 3 is a schematic plan view showing a transfer mechanism of the test piece transfer apparatus of FIG. 1.
Figure 4:
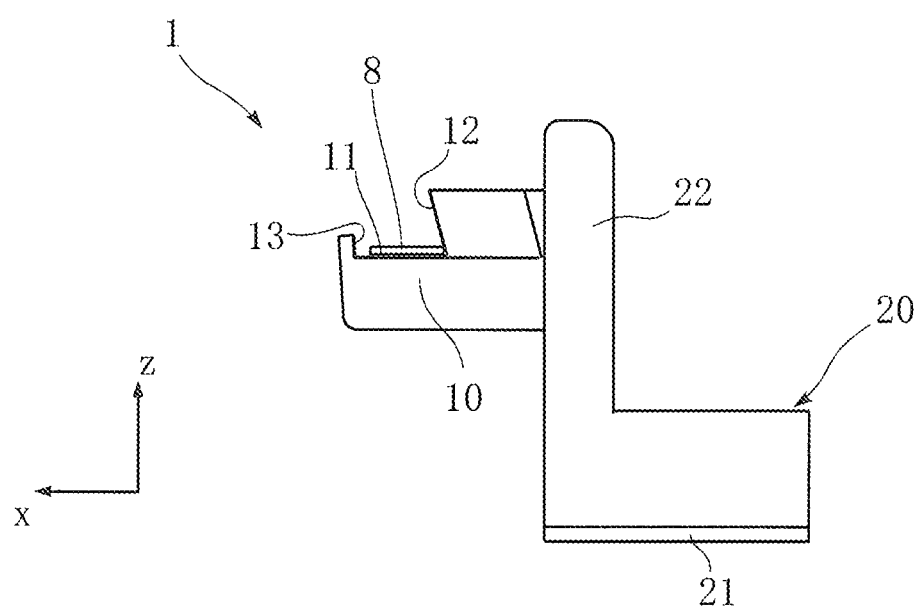
FIG. 4 is a side view showing the transfer mechanism of the test piece transfer apparatus of FIG. 1.

The transfer mechanism 1, configured to transfer a test piece 8 in the direction x, includes a test piece holder 10 and a driving portion 20. In the illustrated example, the test piece holder 10 is made up of two test piece holders (or test piece holding members). FIG. 3 is a plan view of the transfer mechanism 1, and FIG. 4 is a side view of the transfer mechanism 1. The driving portion 20 is caused to move reciprocally in the direction x by a motor (not shown), and includes a bottom portion 21 and two pillar portions 22. The bottom portion 21 is in the form of a rectangle elongated in the direction y as viewed in the direction z, and made of e.g. metal. The two pillar portions 22 stand in the direction z from each end of the bottom portion 21 in the direction y, and may be formed by cutting a metal plate into a predetermined shape. Each pillar portion 22 supports a respective one of the test piece holders 10 at an upper end in the direction z.

The two test piece holders 10 are portions to directly support a test piece 8 and spaced apart from each other in the direction y or along the test piece 8. Each test piece 8 comprises a base material 80, which may mainly be made of paper, and a plurality of reagent regions 81 formed on one side of the base material 80. The test piece 8 is held by the two test piece holders 10 in a manner such that its length extends along the direction y, its width extends along the direction x, and the surface of the base material 80 on which the reagent regions 81 are formed faces upward in the direction z.

Each test piece holder 10 includes a lower surface holding portion 11, an upstream holding portion 12 and a downstream holding portion 13. In the illustrated example, the test piece holder 10 may be made by molding a resin material. Alternatively, the test piece holder 10 may be made of a metal.

The lower surface holding portion 11 comprises the surface of the test piece holder 10 which is oriented upward in the direction z. In the illustrated example, the dimension of the lower surface holding portion 11 in the direction x is larger than the width of the test piece 8 (dimension in the direction x). Further, the dimension of the lower surface holding portion 11 in the direction y is smaller than the dimension of the lower surface holding portion 11 in the direction x and smaller than the width of the test piece 8. The lower surface holding portion 11 may have any suitable configuration as long as it can support or hold a test piece from below. For example, the lower surface holding portion may not comprise a single smooth surface but may comprise a plurality of projections coming into contact with the lower surface of the test piece. Further, the lower surface holding portion may be configured to come into line contact or point contact with the lower surface of the test piece.

The upstream holding portion 12 is positioned on the upstream side of the test piece 8 in the direction x and stands from the upstream end of the lower surface holding portion 11 in the direction x. In this embodiment, as shown in FIG. 4, the upstream holding portion 12 comprises a surface that forms an acute angle with the direction x. Specifically, as shown in FIG. 3, each test piece holder 10 includes a tapered portion that reduces its width as proceeding in the direction x, and the upstream holding portion 12 comprises an end surface of the tapered portion on the downstream side in the direction x. Thus, the dimension of the upstream holding portion 12 in the direction y is smaller than that of the lower surface holding portion 11. The upstream holding portion in the present invention may have any configuration as long as it can hinder the movement of a test piece toward the upstream side in the transfer direction. The upstream holding portion may not comprise a smooth surface but may comprise a plurality of projections that come into contact with the upstream edge of a test piece. Alternatively, the upstream holding portion may be configured to come into line contact or point contact with the upstream edge of a test piece.

The downstream holding portion 13 is positioned on the downstream side of the test piece 8 in the direction x and stands from the downstream end of the lower surface holding portion 11 in the direction x. As shown in FIG. 4, the downstream holding portion 13 comprises a surface that forms a substantially right angle with respect to the direction x. As shown in FIG. 3, the dimension of the downstream holding portion 13 in the direction y is substantially equal to that of the lower surface holding portion 11. The downstream holding portion in the present invention may have any configuration as long as it can hinder the movement of a test piece toward the downstream side in the transfer direction. Thus, the downstream holding portion may not comprise a smooth surface but may comprise a plurality of projections that come into contact with the downstream edge of a test piece. Alternatively, the downstream holding portion may be configured to come into line contact or point contact with the downstream edge of a test piece.

As better shown in FIG. 4, the height of the upstream holding portion 12 from the lower surface holding portion 11 is higher than that of the downstream holding portion 13. As shown in FIG. 3, in this embodiment, the distance between the two test piece holders 10 in the direction y is smaller than the length of the test piece 8 (dimension in the direction y). Each of the test piece holders 10 is arranged to hold the lower surface of the base material 80 at a position where a reagent region 81 is formed.

The base body 3 is made by e.g. molding a resin and has a shape elongated in the direction x as a whole. The base body 3 may serve as an example of a test piece adjusting mechanism of the present invention. As shown in FIG. 1, the base body 3 has two slits 30, two ribs 31, two ribs 32, a center rib 33, four side ribs 34, a first longitudinal position adjusting surface 35a and a second longitudinal position adjusting surface 35b.

The two slits 30 extend in the direction x in parallel to each other and are spaced from each other in the direction y. Each slit 30 allows the pillar portion 22 of the driving portion 20 of the transfer mechanism 1 to pass through the base body 3 from the bottom to the top in the direction z. A rib 31 is provided adjacent to the inner edge of each slit 30, whereas a rib 32 is provided adjacent to the outer edge of each slit 30.

Each rib 31 projects in the direction z from a position adjacent to the slit 30 and is elongated in the direction x. The rib 31 includes a receiving portion 31a, a flat portion 31b and a raised portion 31c. The receiving portion 31a is a portion positioned adjacent to the upstream end of the rib 31 in the direction x, facing upward in the direction z and extending in parallel to the direction x. As shown in FIG. 2, the position of the receiving portion 31a in the direction z is slightly higher than the lower surface holding portion 11 of the transfer mechanism 1. The receiving portion 31a serves to receive a test piece 8 fed to the transfer apparatus A1. The position where a test piece is received by the receiving portion 31a is the receiving point 36a.

The flat portion 31b is provided on the downstream side of the receiving portion 31a in the direction x, faces upward in the direction z and extends in parallel to the direction x. The position of the flat portion 31b in the direction z is lower than that of the receiving portion 31a and also lower than that of the lower surface holding portion 11 of the transfer mechanism 1. The raised portion 31c is provided on the downstream side of the flat portion 31b in the direction x. The raised portion 31c is made up of a portion facing upward in the direction z and extending in parallel to the direction x and an inclined portion connecting this portion and the flat portion 31b to each other. The position of the raised portion 31c in the direction z is higher than that of the flat portion 31b and also higher than that of the lower surface holding portion 11 of the transfer mechanism 1. The raised portion 31c overlaps the position control finishing point 36b where positioning of the test piece 8 in the transfer process is completed. Of the rib 31, the portion which is positioned between the flat portion 31b and the position control finishing point 36b in the direction x and which is higher than the lower surface holding portion 11 in the direction z functions as the raised portion 31c.

The rib 32 projects in the direction z from a position adjacent to the slit 30 and on the opposite side of the rib 31, and is elongated in the direction x. The rib 32 includes a flat portion 32b and a raised portion 32c. The position of the flat portion 32b in the direction z is the same as that of the flat portion 31b of the rib 31. In the direction x, the flat portion 32b is provided at a position that overlaps the flat portion 31b and the receiving portion 31 of the rib 31. The raised portion 32c is provided on the downstream side of the flat portion 32b in the direction x. The position and shape of the raised portion 32c as viewed in the direction y are the same as those of the raised portion 31c of the rib 31.

The center rib 33 is provided adjacent to the center of the base body 3 in the direction y and sandwiched between the two ribs 31 and the two ribs 32. Similarly to the ribs 31 and 32, the center rib 33 is elongated in the direction x. The position and shape of the center rib 33 as viewed in the direction y are the same as those of the raised portions 31c and 32c of the ribs 31 and 32.

The four side ribs 34 are elongated in the direction x and arranged in parallel to each other while being spaced apart from each other in the direction y. Two of the side ribs 34 are arranged between the two ribs 31 and the center rib 33. The remaining two of the side ribs 34 are arranged on the outer side of the two ribs 32 in the direction y. The upper end of each of the four side ribs 34 is at the same position in the direction z as the upper ends of the raised portions 31c, 32c of the ribs 31, 32 and overlaps the position control finishing point 36b in the direction x. Of the four side ribs 34, the portions higher than the lower surface holding portion 11 of the transfer mechanism 1 cover an area in the direction x which is smaller than the area covered by the raised portions 31c, 32c of the ribs 31, 32. In this way, each of the four ribs 34 includes a portion higher than the lower surface holding portion 11 in the direction z, though the area covered by this portion in the direction x is smaller than that covered by the raised portions 31c, 32c.

The first longitudinal position adjusting surface 35a is provided at a first side of the base body 3 in the direction y, as a wall surface standing in the direction z and facing inward in the direction y. The first longitudinal position adjusting surface 35a is inclined to come closer to the other or second side (opposite to the first side in the direction y) as proceeding from the upstream side toward the downstream side in the direction x.

The second longitudinal position adjusting surface 35b is provided at the second side of the base body 3 in the direction y as a wall surface standing in the direction z and facing inward in the direction y. The second longitudinal position adjusting surface 35b is inclined to come closer to the first side in the direction y as proceeding from the upstream side toward the downstream side in the direction x. The area covered by the second longitudinal position adjusting surface 35b in the direction x is smaller than the area covered by the first longitudinal position adjusting surface 35a and overlaps an upstream portion in the direction x of the area covered by the first longitudinal position adjusting surface 35a.

Referring to FIG. 1, the section in which the first longitudinal position adjusting surface 35a and the second longitudinal position adjusting surface 35b face each other is defined as a first adjusting section 37a. The section in which only the first longitudinal position adjusting surface 35a exists and the second longitudinal position adjusting surface 35b does not exist is defined as a second adjusting section 37b.

In this embodiment, at the downstream end of the first adjusting section 37a in the direction x, the distance between the second longitudinal position adjusting surface 35b and the center of the transfer mechanism 1 in the direction y corresponds to half the dimension of the test piece 8 in the direction y. On the other hand, at the downstream end of the first adjusting section 37a in the direction x, the distance between the first longitudinal position adjusting surface 35a and the center of the transfer mechanism 1 in the direction y is slightly longer than half the dimension of the test piece 8 in the direction y. At the downstream end of the second adjusting section 37b in the direction x, the distance between the first longitudinal position adjusting surface 35a and the center of the transfer mechanism 1 in the direction y corresponds to half the dimension of the test piece 8 in the direction y.

The operation for transferring a test piece 8 by the transfer apparatus A1 is described below.

First, of a plurality of test pieces 8 stored (not shown), the one arranged at the bottom in the direction z is supplied to the transfer apparatus A1. Specifically, the test piece 8 is supplied when the transfer mechanism 1 is at the most upstream position in the direction x as shown in FIG. 1, with the two test piece holders 10 positioned at the receiving point 36a. The test piece 8 is supplied to a position overlapping the lower surface holding portions 11 of the two test piece holders 10 at the receiving point 36a. However, since the receiving portions 31a of the two ribs 31 are positioned above the lower surface holding portion 11 in the direction z as shown in FIG. 2, the test piece 8 is received by the two receiving portions 31a.

Then, the transfer mechanism 1 starts to move downstream in the direction x. Specifically, the test piece 8 is pushed at two positions spaced apart from each other in the direction y by the upstream holding portions 12 of the two test piece holders 10 toward the downstream side in the direction x. Thus, the test piece 8 is transferred while keeping the posture parallel to the direction y and without improperly turning around an axis extending in the direction z. When the test piece 8 is transferred to a position that does not overlap the receiving portion 31a in the direction x, the test piece 8, which has been held on the receiving portion 31a, moves onto the lower surface holding portions 11 of the test piece holders 10 and held on the lower surface holding portions 11.

Figure 5:
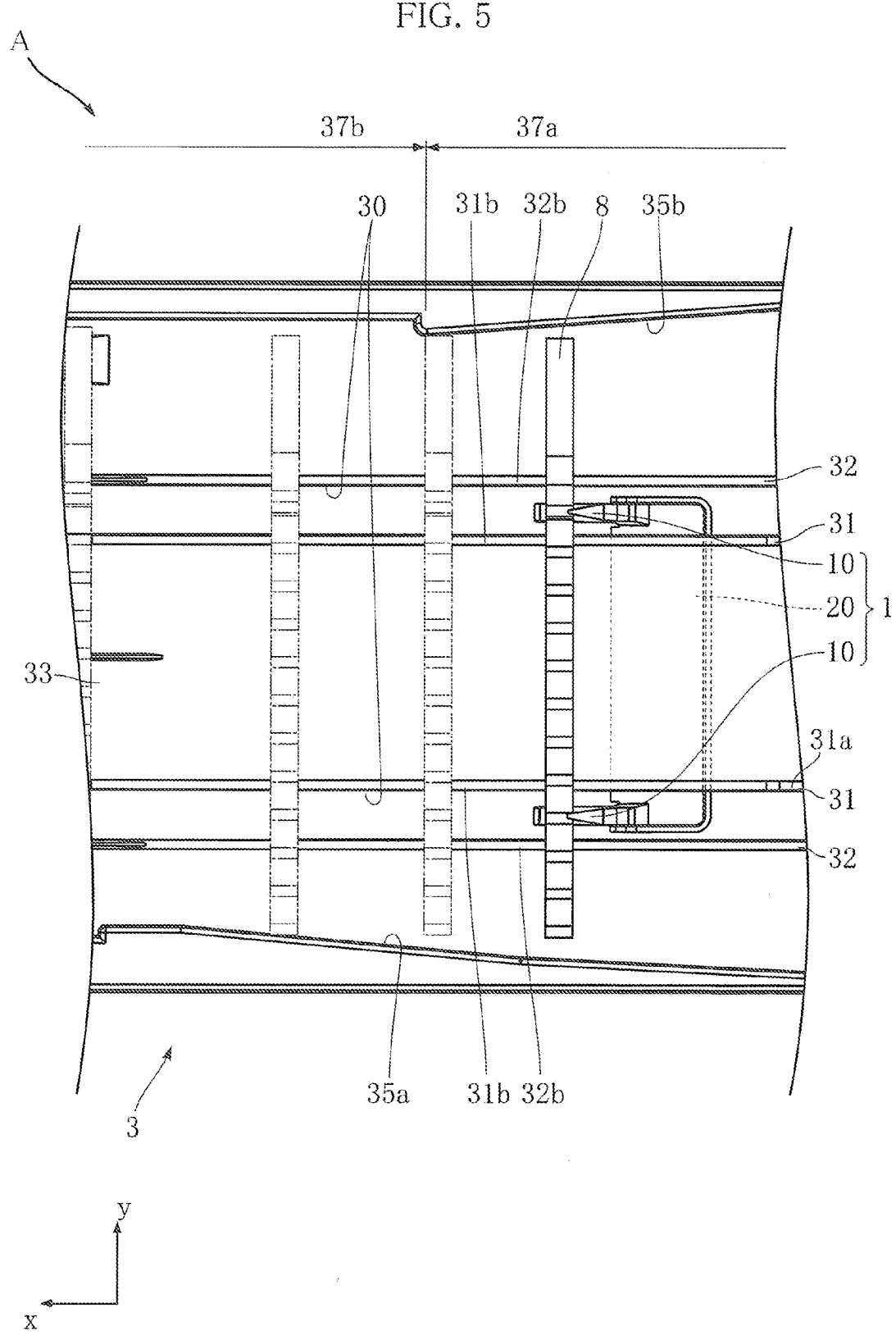
FIG. 5 is a schematic plan view showing the test piece transfer process by the test piece transfer apparatus of FIG. 1.

Then, as shown in FIG. 5, the test piece 8 is transferred by the transfer mechanism 1 downstream in the direction x through the first adjusting section 37a. In the first adjusting section 37a, the first longitudinal position adjusting surface 35a and the second longitudinal position adjusting surface 35b exist on the outer sides of the test piece 8 in the direction y. Thus, for instance, when the test piece 8 is supplied to a position deviated from a predetermined position toward the second side in the direction y, the end of the test piece 8 at the second side in the direction y comes into contact with the second longitudinal position adjusting surface 35b. In this embodiment, at the downstream end of the first adjusting section 37a in the direction x, the distance between the center of the transfer mechanism 1 in the direction y and the second longitudinal position adjusting surface 35b is half the dimension of the test piece 8 in the direction y, and the distance between the center of the transfer mechanism 1 in the direction y and the first longitudinal position adjusting surface 35a is longer than this. Thus, as shown in FIG. 5, the test piece 8 reaching the downstream end of the first adjusting section 37a in the direction x comes into contact with the longitudinal position adjusting surface 35b at its end at the second side in the direction y. On the other hand, when the test piece 8 is supplied to a position deviated from a predetermined position toward the first side in the direction y, the end of the test piece 8 at the first side in the direction y comes into contact with the first longitudinal position adjusting surface 35a. When the test piece 8 reaches, as it is, the downstream end in the direction x of the first adjusting section 37a, the end of the test piece 8 at the first side in the direction y is still in contact with the first longitudinal position adjusting surface 35a.

Figure 6:
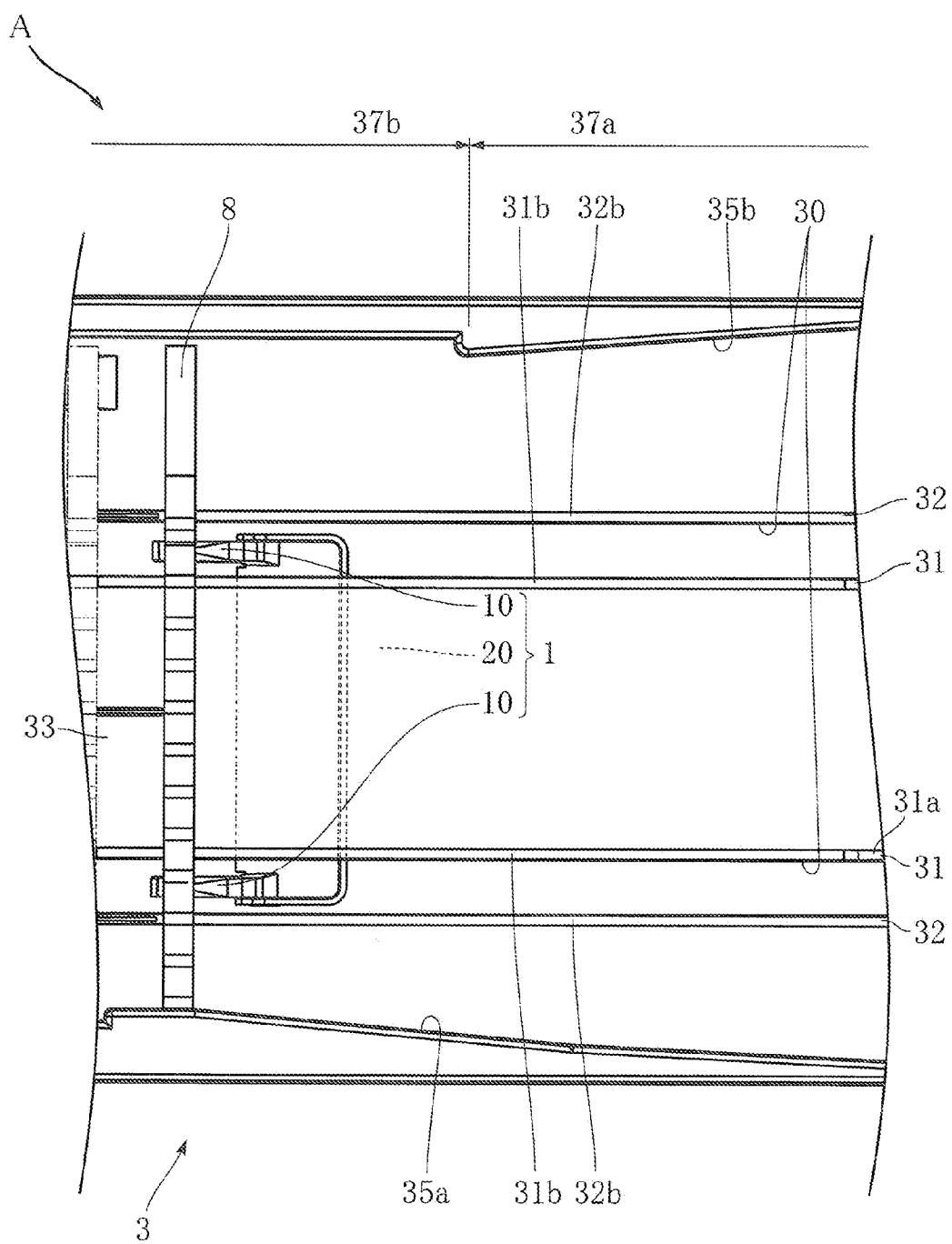
FIG. 6 is a schematic plan view showing the test piece transfer process by the test piece transfer apparatus of FIG. 1.

As the test piece 8 is transferred further downstream in the direction x by the transfer mechanism 1, the test piece 8 enters the second adjusting section 37b. In the second adjusting section 37b, only the first longitudinal position adjusting surface 35a exists, and the second longitudinal position adjusting surface 35b does not exist. Thus, in the case where the end of the test piece 8 at the second side in the direction y was in contact with the longitudinal position adjusting surface 35b at the downstream end in the direction x of the first adjusting section 37a, the test piece 8 becomes separated from both the first longitudinal position adjusting surface 35a and the second longitudinal position adjusting surface 35b when entering the second adjusting section 37b. When the test piece 8 is transferred further downstream in the direction x through the second adjusting section 37b, the end of the test piece 8 at the first side comes into contact with the first longitudinal position adjusting surface 35a. Thereafter, when the test piece 8 reaches the downstream end of the second adjusting section 37b in the direction x as shown in FIG. 6, the center of the test piece 8 in the direction y and the center of the transfer mechanism 1 in the direction y correspond to each other. On the other hand, in the case where the end of the test piece 8 at the first side in the direction y was in contact with the first longitudinal position adjusting surface 35a at the downstream end of the first adjusting section 37a in the direction x, the test piece 8 is gradually moved by the first longitudinal position adjusting surface 35a from the first side toward the second side in the direction y while being transferred downstream through the second adjusting section 37b. When the test piece 8 reaches the downstream end of the second adjusting section 37b in the direction x, the center of the test piece 8 in the direction y and the center of the transfer mechanism 1 in the direction y correspond to each other. In this way, by passing test piece 8 through the first adjusting section 37a and the second adjusting section 37b, positioning of the test piece 8 in the direction y is completed. In this positioning process, the upstream holding portions 12 and the downstream holding portions 13 of the two test piece holders 10 properly prevent the test piece 8 from turning around an axis extending in the direction z.

Figure 7:
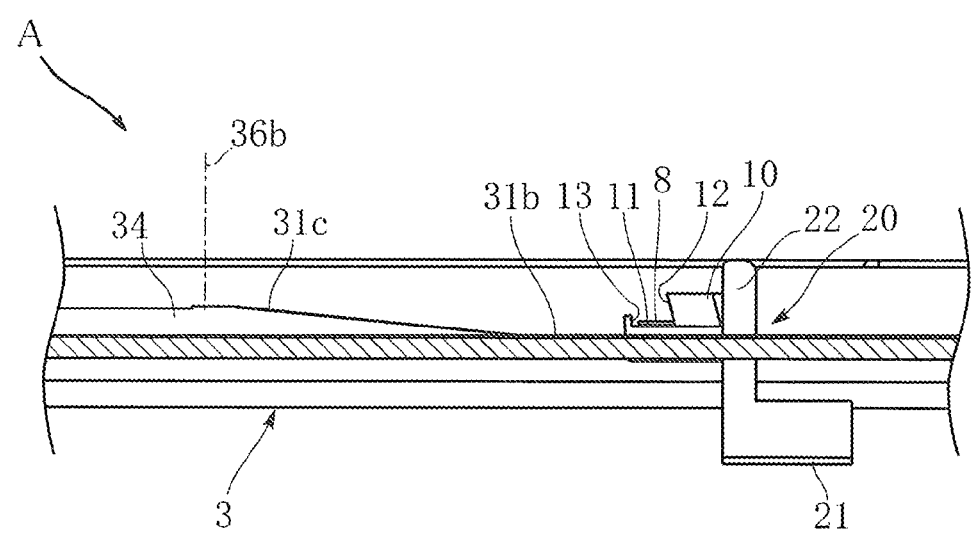
FIG. 7 is a schematic sectional view showing the test piece transfer process by the test piece transfer apparatus of FIG. 1.
Figure 8:
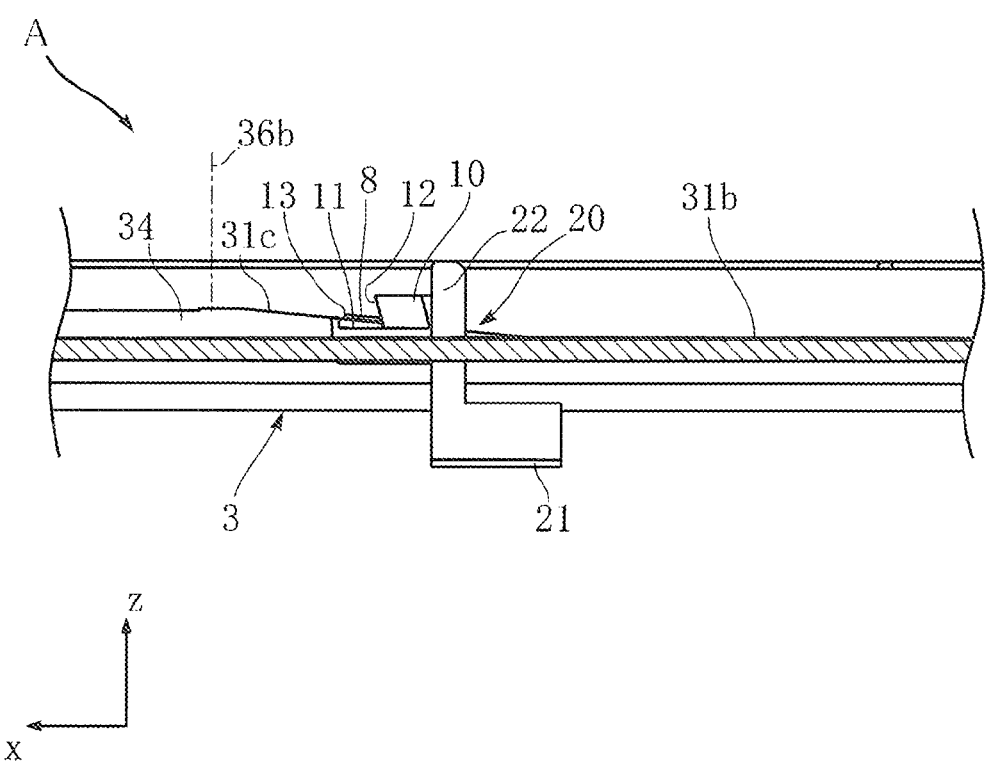
FIG. 8 is a schematic sectional view showing the test piece transfer process by the test piece transfer apparatus of FIG. 1.

As shown in FIG. 7, after passing through the second adjusting section 37b, the test piece 8 is positioned on the upstream side of the raised portion 31c of the rib 31. Although only the raised portion 31c of the rib 31 is shown in FIG. 7, the raised portion 32c of the rib 32 has the same shape as that of the raised portion 31c of the rib 31 and is provided at the same position as the raised portion 31c of the rib 31 as viewed in the direction y. When the test piece 8 is transferred downstream in the direction x from the state shown in FIG. 7, the lower surface of the test piece 8 comes into contact with the raised portion 31c (and the raised portion 32c), as shown in FIG. 8.

As the test piece 8 is transferred further downstream in the direction x, the lower surface of the test piece 8 separates from the lower surface holding portions 11 of the two test piece holders 10 and is held on the raised portion 31c (and the raised portion 32c). As the transfer mechanism 1 in this sate moves downstream in the direction x, the test piece 8 is pushed by the upstream holding portion 12 of the two test piece holders 10 downstream in the direction x while being held on the raised portion 31c (and the raised portion 32c). Since the test piece 8 comes into contact with the slant portion of the raised portion 31c (and the raised portion 32c) in this process, the front edge of the test piece 8 may rise, depending on the transfer speed and so on. However, since the upstream holding portions 12 of the two test piece holders 10 are in the form of a wall that forms an acute angle with the direction x, the test piece 8 is prevented from standing or turning over. Thereafter, when the test piece 8 reaches the position control finishing point 36b, the test piece 8 is held by the raised portion 31c, 32c of the ribs 31,32, the center rib 33, and the four side ribs 34. In this way, positioning of the test piece 8 in the direction z is completed.

As described above, when the test piece 8 is transferred to the position control finishing point 36b, positioning of the test piece 8 in the direction y and in the direction z is completed. Thereafter, the test piece 8 is subjected to processing in the next step. Examples of the process step subsequent to the above-described transferring step include e.g. checking whether or not the reagent regions 81 are in proper condition, applying urine as a specimen to the test piece 8, and further transfer of the test piece 8 to a specimen application mechanism (not shown) provided separately from the transfer apparatus. All of these process steps can be performed properly because the test piece 8 is positioned properly at the position control finishing point 36b.

The advantages of the transfer apparatus A1 are described below.

According to this embodiment, the test piece 8 is transferred, with the upstream holding portion 12 positioned on the upstream side of the test piece 8 in the direction x and the downstream holding portion 13 positioned on the downstream side of the test piece 8 in the direction x, while being held by the lower surface holding portions 11. Thus, the test piece 8 is prevented from turning around an axis extending in the direction z. Especially, turning of the test piece 8 is prevented even when paper powder or dust is accumulated on the base body 3. Thus, the test piece 8 is smoothly transferred without positional deviation.

Figure 10:
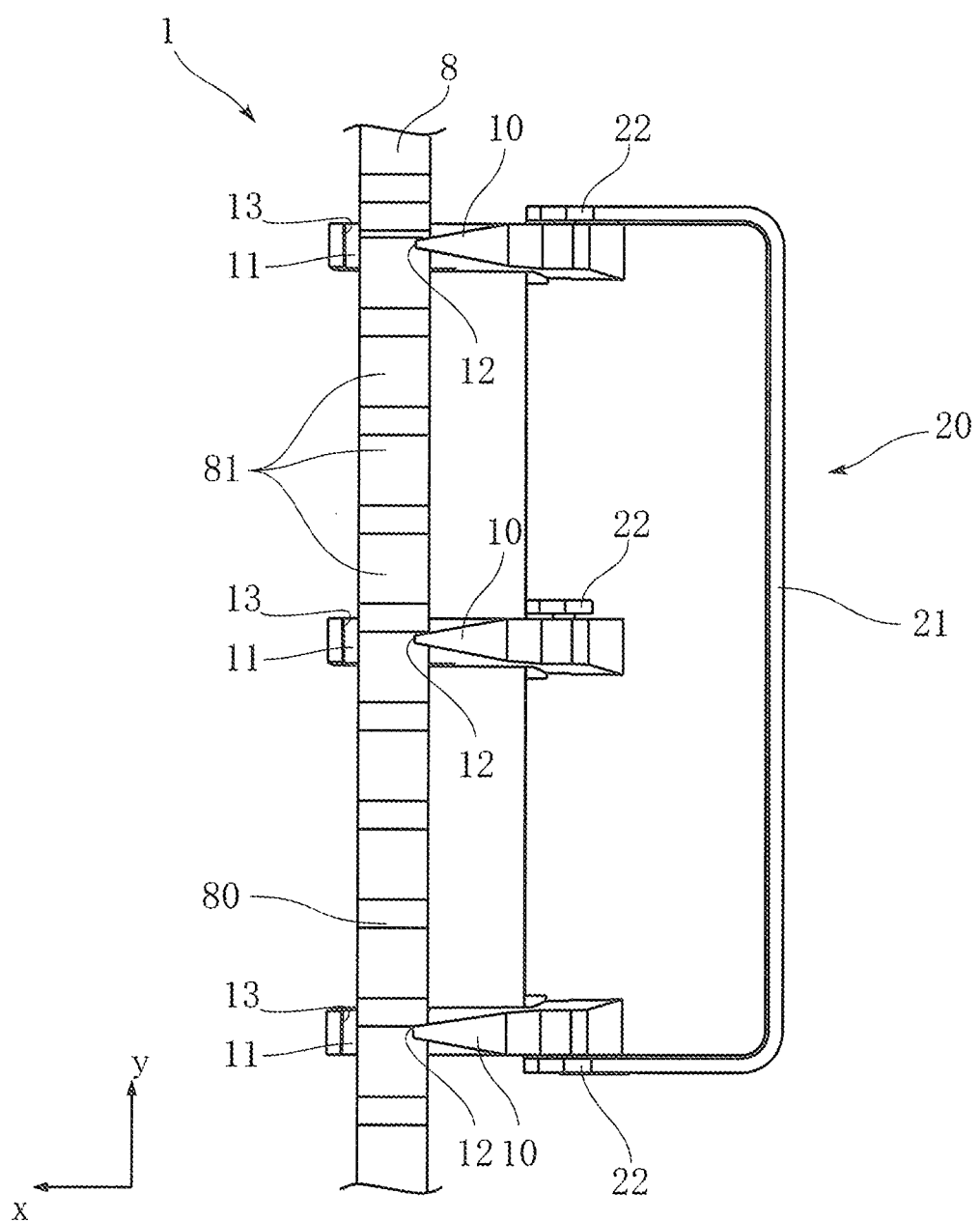
FIG. 10 is a schematic plan view showing another example of transfer mechanism of the test piece transfer apparatus.
Figure 11:
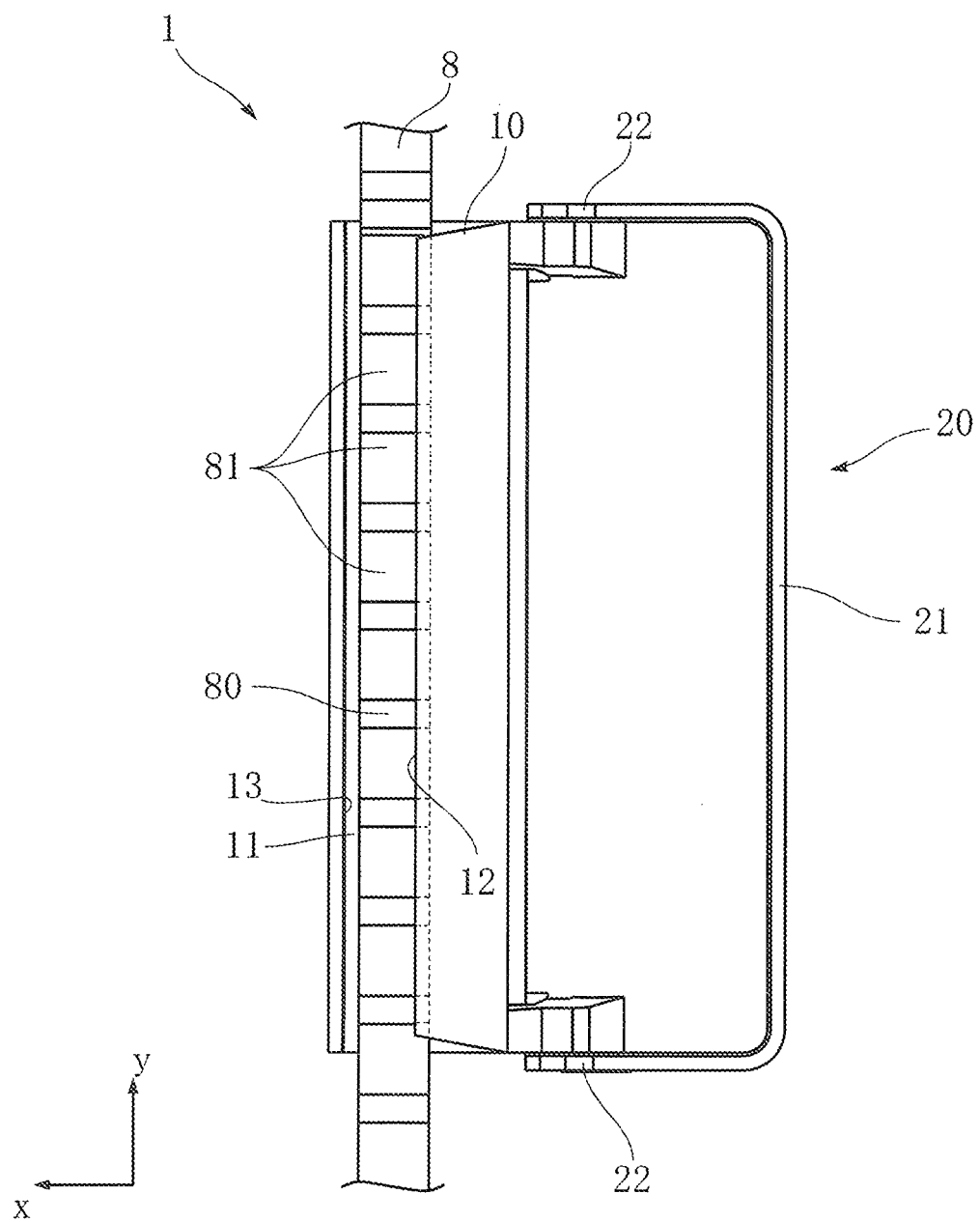
FIG. 11 is a schematic plan view showing another example of transfer mechanism of the test piece transfer apparatus.

Provision of the two test piece holders 10 spaced apart from each other in the direction y, which corresponds to the longitudinal direction of the test piece 8, also helps to reliably prevent the test piece 8 from turning around an axis extending in the direction z. The two test piece holders 10 are arranged at positions relatively close to the center of the test piece 8. This arrangement allows many kinds of test pieces 8 of different lengths to be held properly by the test piece holders 10. In the present invention, the number of the test piece holders 10 is not limited to two. That is, the transfer apparatus may include three test piece holders 10 as shown in FIG. 10 or four or more test piece holders 10. Alternatively, as shown in FIG. 11, a single test piece holder 10 may be used in which all of the lower surface holding portion 11, the upstream holding portion 12 and the downstream holding portion 13 are elongated in the direction y. With this arrangement again, proper transfer of the test piece 8 without positional deviation is achieved.

Since the upstream holding portion 12 forms an acute angle with the direction x, even if the front edge of the test piece 8 rises during the transferring operation, the test piece 8 is prevented from standing or turning over. This is especially advantageous when the transfer speed by the transfer mechanism 1 is increased.

Figure 9:
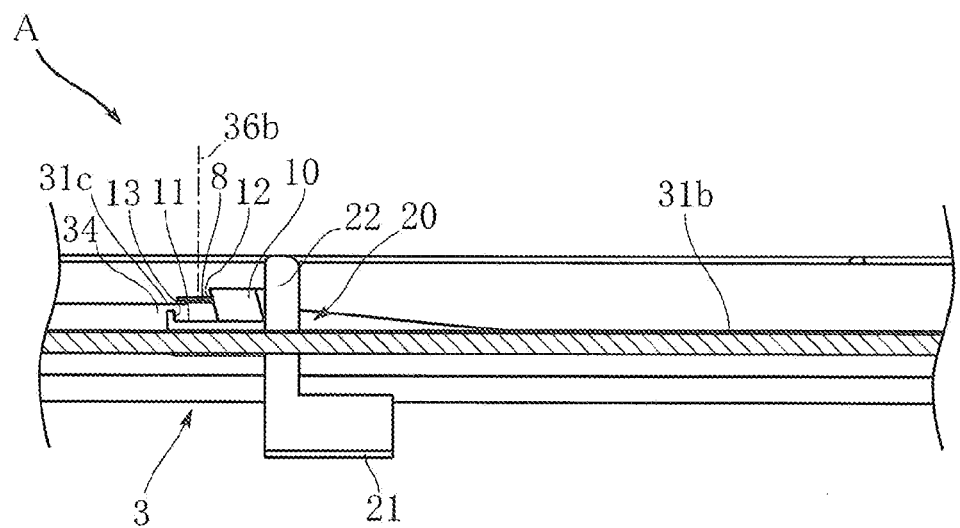
FIG. 9 is a schematic sectional view showing the test piece transfer process by the test piece transfer apparatus of FIG. 1.

As described with reference to FIGS. 7-9, raised portions 31c and 32c are provided, and the upper end of the upstream holding portion 12 is positioned higher than the raised portions 31c and 32c in the direction z. This arrangement assures proper positioning of the test piece 8 in the direction z in the transfer process. Moreover, the raised portions 31c and 32c are higher than the upper end of the downstream holding portion 13 in the direction z. Thus, at or adjacent to the position control finishing point 36b, the downstream holding portion 13 does not come into contact with the downstream edge of the test piece 8 in the direction x, so that movement of the test piece 8 downstream in the direction x is not hindered by the downstream holding portion 13. Thus, the test piece 8 can be smoothly transferred to the subsequent process step.

The transfer apparatus includes, in addition to the raised portions 31c and 32c, the center rib 33 and four side ribs 34. Thus, at the position control finishing point 36b where the test piece 8 is released from the lower surface holding portion 11, the test piece 8 is held at a wide region not only by the two raised portions 31c, 32c but also by the center rib 33 and the four side ribs 34. Thus, in the case where the subsequent process using the test piece 8 is to be performed at the position control finishing point 36b, the process can be performed properly without twisting or bending of the test piece 8.

As described with reference to FIGS. 5 and 6, the test piece 8 is properly positioned in the direction y by the first longitudinal position adjusting surface 35a and the second longitudinal position adjusting surface 35b. In the first adjusting section 37a, the first longitudinal position adjusting surface 35a and the second longitudinal position adjusting surface 35b are inclined to reduce the gap between them as proceeding downward in the direction x. With this arrangement, positioning of the test piece 8 is performed smoothly. Owing to the provision of the second adjusting section 37b connected to the first adjusting section 37a, the test pieces 8 supplied as deviated toward the first side or the second side in the direction y or test pieces 8 of different lengths can be positioned properly.

Figure 12:
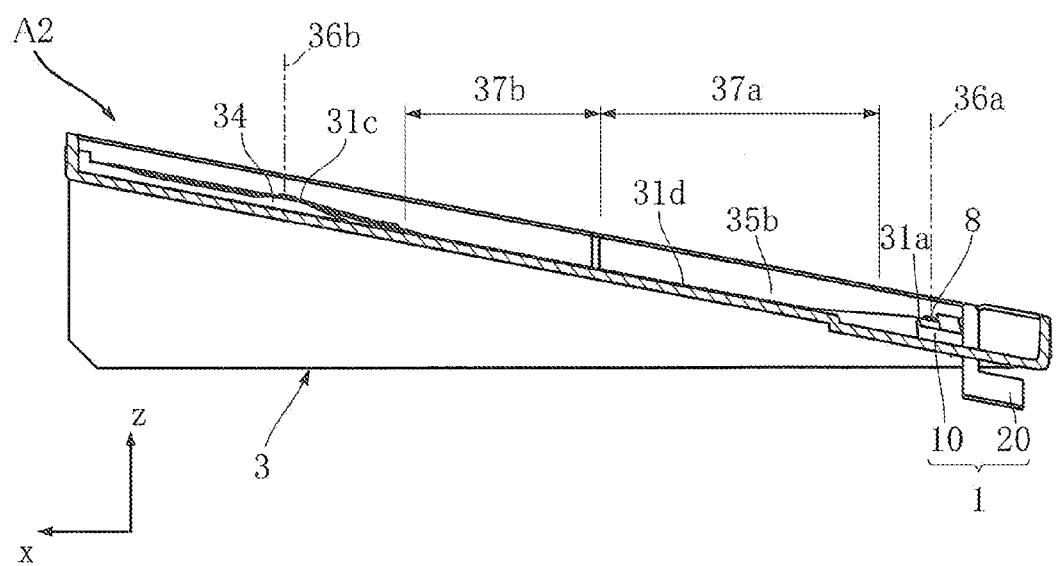
FIG. 12 is a sectional view showing a test piece transfer apparatus according to a second embodiment of the present invention.
Figure 13:
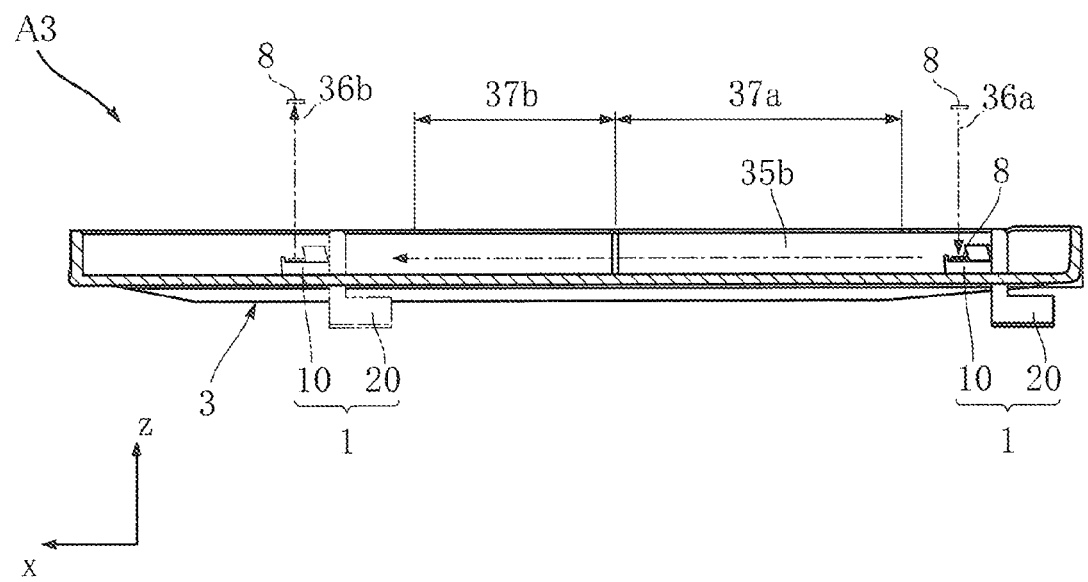
FIG. 13 is a sectional view showing a test piece transfer apparatus according to a third embodiment of the present invention.
Figure 14:
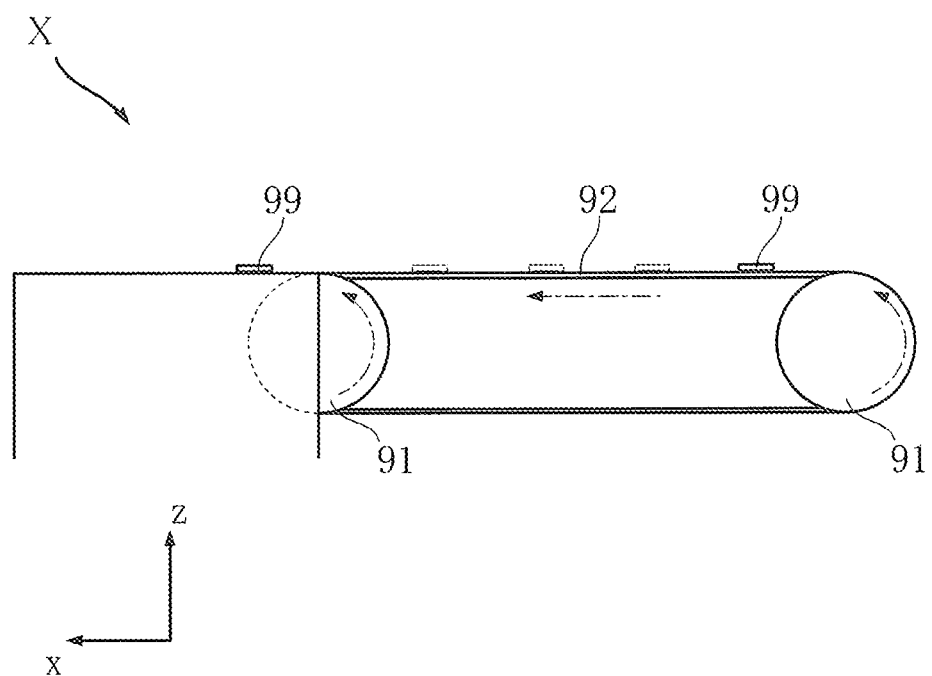
FIG. 14 is a side view showing an example of conventional test piece transfer apparatus.

FIGS. 12 and 13 show other embodiments of the present invention. In these figures, the elements that are identical or similar to those of the foregoing embodiment are designated by the same reference signs as those used for the foregoing embodiment.

FIG. 12 shows a test piece transfer apparatus according to a second embodiment of the present invention. In the illustrated test piece transfer apparatus A2, the movement path of the transfer mechanism 1 from the receiving point 36a to the position control finishing point 36b is inclined with respect to the direction x. That is, in the case where the direction z corresponds to the vertical direction, the transfer mechanism 1 gradually moves up as proceeding from the receiving point 36a to the position control finishing point 36b.

The rib 31 includes a slant portion 31d between a receiving portion 31a and a raised portion 31c. The slant portion 31d is inclined with respect to the direction x. Of the slant portion 31d, the portion which overlaps the lower surface holding portion 11 of the test piece holder 10 in the direction x during the movement of the transfer mechanism 1 is positioned lower than the lower surface holding portion 11 in the direction z. According to this embodiment again, the test piece 8 is transferred smoothly without positional deviation.

FIG. 13 shows a test piece transfer apparatus according to a third embodiment of the present invention. The test piece transfer apparatus A3 of this embodiment does not include the ribs 31, 32, the center rib 33 and the side ribs 34 of the foregoing embodiments.

In the illustrated transfer apparatus A3, a test piece 8 is fed at the receiving point 36a to the test piece holder 10 of the transfer mechanism 1 by e.g. a test piece feeding mechanism, not shown. The test piece holder 10 receives the test piece 8. By the movement of the transfer mechanism 1 to the left in the direction x in FIG. 13, positioning of the test piece 8 in its longitudinal direction of the test piece 8, i.e., in the direction y is completed. Then, the transfer mechanism 1 reaches the position control finishing point 36b. At the position control finishing point 36b, the test piece 8 is picked up from the test piece holder 10 by a test piece picking mechanism, not shown. According to this embodiment again, the test piece 8 is smoothly transferred without positional deviation.

The test piece transfer apparatus of the present invention is not limited to the foregoing embodiments. The specific structure of each part of the test piece transfer apparatus according to the present invention can be varied in design in many ways.

The test piece transfer apparatus of the present invention is capable of properly transferring various kinds of test pieces in the form of a strip. Thus, test pieces for the tests other than urine qualitative analysis can also be an object to be transferred. The test piece transfer apparatus of the present invention may be designed to perform only the test piece transfer operation or may be designed to constitute an analyzer together with an analysis unit for performing analysis.

The invention claimed is:

1. A test piece transfer apparatus comprising:
   a transfer mechanism for transferring an elongated test piece in a transfer direction corresponding to a width direction of the test piece, the transfer mechanism being provided with a test piece holder for holding the test piece and with a driving portion; and
   a test piece adjusting mechanism cooperating with the transfer mechanism for adjusting a direction of the test piece;
   wherein the test piece holder includes: a test piece holding member comprising a lower surface holding portion for coming into contact with a lower surface of the test piece; an upstream holding portion arranged on an upstream side of the test piece in the transfer direction; and a downstream holding portion arranged on a downstream side of the test piece in the transfer direction; and
   wherein the test piece adjusting mechanism includes a flat portion and a raised portion arranged on a downstream side of the flat portion in the transfer direction,
   the flat portion is at a lower position than the lower surface holding portion, and the raised portion is raised above the lower surface holding portion.

2. The test piece transfer apparatus according to claim 1, wherein the test piece holder comprises a plurality of test piece holding members spaced apart from each other along the test piece.

3. The test piece transfer apparatus according to claim 1, wherein the test piece holder comes into holding contact with the test piece at a position spaced apart from each of two ends of the test piece.

4. The test piece transfer apparatus according to claim 1, wherein the upstream holding portion comprises a wall surface facing the test piece, the wall surface forming an acute angle with respect to the transfer direction.

5. The test piece transfer apparatus according to claim 1, wherein the downstream holding portion is smaller in height than the upstream holding portion, and the raised portion is raised to a point that is higher than the downstream holding portion and lower than an upper end of the upstream holding portion.

6. The test piece transfer apparatus according to claim 1, wherein the test piece holder comprises two test piece holding members spaced apart from each other along the test piece with a center of the test piece being sandwiched by the two test piece holding members, and the raised portion is arranged between the two test piece holding members.

7. The test piece transfer apparatus comprising:
   a transfer mechanism for transferring an elongated test piece in a transfer direction corresponding to a width direction of the test piece, the transfer mechanism being provided with a test piece holder for holding the test piece and with a driving portion; and
   a test piece adjusting mechanism cooperating with the transfer mechanism for adjusting a direction of the test piece;
   wherein the test piece holder includes: a test piece holding member comprising a lower surface holding portion for coming into contact with a lower surface of the test piece; an upstream holding portion arranged on an upstream side of the test piece in the transfer direction; and a downstream holding portion arranged on a downstream side of the test piece in the transfer direction;
   wherein the test piece adjusting mechanism is provided with a first position adjusting section and a second position adjusting section disposed on a downstream side of the first position adjusting section in the transfer direction, and with a first and a second longitudinal position adjusting surfaces spaced apart from each other in a longitudinal direction of the test piece,
   in the first position adjusting section, the first longitudinal position adjusting surface and the second longitudinal position adjusting surface face each other in such a manner that a distance between the first and the second longitudinal position adjusting surfaces reduces as proceeding downward in the transfer direction,
   the first longitudinal position adjusting surface is present in the second position adjusting section, and the second longitudinal position adjusting surface as a whole is disposed out of the second longitudinal position adjusting surface.

8. The test piece transfer apparatus according to claim 7, wherein each of the first and the second longitudinal position adjusting surfaces is inclined with respect to the transfer direction.

9. The test piece transfer apparatus according to claim 7, wherein a flat portion is arranged to overlap, along the transfer direction, at least one of the first position adjusting section and the second position adjusting section, and
   a raised portion includes a part that is positioned on the downstream side of the second position adjusting section in the transfer direction so as not to overlap the second position adjusting section.

* * * * *